(12) United States Patent
Bartels et al.

(10) Patent No.: US 9,662,130 B2
(45) Date of Patent: May 30, 2017

(54) SURGICAL FORCEPS WHICH CAN BE TAKEN APART

(75) Inventors: Carolin Bartels, Barmstedt (DE);
Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 14/115,246

(22) PCT Filed: Apr. 19, 2012

(86) PCT No.: PCT/EP2012/057189
§ 371 (c)(1),
(2), (4) Date: Nov. 1, 2013

(87) PCT Pub. No.: WO2013/156071
PCT Pub. Date: Oct. 24, 2013

(65) Prior Publication Data
US 2014/0088639 A1    Mar. 27, 2014

(51) Int. Cl.
*A61B 17/00*    (2006.01)
*A61B 17/28*    (2006.01)
*A61B 90/00*    (2016.01)

(52) U.S. Cl.
CPC ...... *A61B 17/2816* (2013.01); *A61B 17/2833* (2013.01); *A61B 2090/0813* (2016.02)

(58) Field of Classification Search
CPC ............ A61B 17/2816; A61B 17/2947; A61B 17/2833; A61B 2019/4868; A61B 17/1227; A61B 2090/0813; A61B 90/30; B25B 7/08; B25B 7/06; B25B 7/18; B25B 7/10; B25B 7/02; B25B 7/14; B25B 7/22; B25B 9/00; A61C 7/14; A61C 7/04; A61C 7/02
(Continued)

(56) References Cited

U.S. PATENT DOCUMENTS 168,012 A  * 9/1875 Gaillard ..................... 433/146
1,475,569 A    11/1923 Dondero
(Continued)

FOREIGN PATENT DOCUMENTS

DE    10 2009 003    11/2010
EP    2 508 140    10/2012

OTHER PUBLICATIONS

International Search Report and Written Opinion mailed Feb. 13, 2013, directed to International Application No. PCT/EP2012/057189; 11 pages.

*Primary Examiner* — Katherine M Shi
*Assistant Examiner* — Mohamed Gabr
(74) *Attorney, Agent, or Firm* — Morrison & Foerster LLP

(57) ABSTRACT

A pair of surgical forceps which can be taken apart and which includes a handle, a pivot joint with a rotational axis and a jaw. It further includes two releasably coupled forceps parts, each of which has a pin-less pivot joint element. The first pivot joint element has a first guide rail and a first guide recess. The second pivot joint element has a second guide rail and a second guide recess. The guide rails, which engage in an undercut of the guide recesses on the pivot joint elements, form a sliding guide for the pivot joint. The first pivot joint element has a first thickening element and the second pivot joint element has a second surface element. In a safety position the first thickening element interacts with the second surface element by means of jamming.

14 Claims, 6 Drawing Sheets

(58) Field of Classification Search
USPC ............... 606/205, 207, 208; 81/416, 417; 433/159, 146, 4, 153, 157; 362/119
See application file for complete search history.

(56) References Cited

U.S. PATENT DOCUMENTS

| | | | |
|---|---|---|---|
| 2,611,288 A * | 9/1952 | Schiffbauer | 81/416 |
| 2,632,661 A | 3/1953 | Cristofv | |
| 3,982,450 A * | 9/1976 | Marsh | 81/416 |
| 4,932,955 A * | 6/1990 | Merz | A61B 17/1227 24/510 |
| 5,197,879 A * | 3/1993 | Fowler et al. | 433/159 |
| 5,232,360 A * | 8/1993 | Ingels | 433/4 |
| 7,399,101 B2 * | 7/2008 | Clausen et al. | 362/119 |
| 8,210,845 B1 * | 7/2012 | Ingels | 433/4 |
| 8,273,096 B2 * | 9/2012 | Lazic | 606/158 |
| 2010/0298849 A1 | 11/2010 | Lazic | |

\* cited by examiner

SURGICAL FORCEPS WHICH CAN BE TAKEN APART

REFERENCE TO RELATED APPLICATIONS

This application is a national stage application under 35 USC 371 of International Application No. PCT/EP2012/057189, filed Apr. 19, 2012, the entire contents of which are incorporated herein by reference.

FIELD OF THE INVENTION

The invention relates to a pair of surgical forceps which can be taken apart and which has a pivot joint element with a thickening element.

BACKGROUND OF THE INVENTION

Tools with a gripping or cutting function such as, for example, scissors or forceps are used in many areas. As a rule, said tools consist of two parts which are connected together by means of a screw. If said two parts need to be cleaned, which among other things is necessary in medical application, the screw has to be undone. In addition, the surgical instrument has to meet the demands of the operation. The instrument, in particular surgical forceps, has to be sturdy, functional and easy to handle. In addition, it should have a resilient end position in order to limit the force onto the held objects. Part of the easy handling is the rapid and simple dismantling of the surgical instrument. This is necessary so that the surgical instrument is able to be disinfected and cleaned in an autoclave.

The usual design of surgical scissors or forceps includes many small parts, the forceps parts being held together by screw or pin connections. Prior to disinfection and cleaning, the instrument has to be taken apart laboriously. After disinfection and cleaning the surgical instrument has to be put back together again laboriously. If small parts are lost, assembly is no longer possible and the instrument is no longer available for the next operation. For this reason tools have been developed which are easily able to be broken down into their individual parts. Said tools include two individual parts which are releasable without a further tool.

U.S. Pat. No. 2,632,661 discloses a pivot joint for a pair of scissors or forceps, one pivot part including a guide rail which is able to be coupled into a guide groove of the other pivot part. The coupling of the two pivot parts is only possible with the joint at a certain angle of opening. At said angle of opening, the guide rails of the one pivot part are no longer encompassed by the guide groove of the other pivot joint, the two pivot parts being able to be released in said position. The disadvantage of said apparatus is that the guide grooves are only able to be cleaned in a very poor manner as they are very deep and narrow. Thus, for example, tissue parts or tissue fluids are able to be deposited in said grooves such that bacteria and viruses are able to reproduce there or said bacteria and viruses are not able to be killed off even in a disinfecting autoclave. In addition, said apparatus has the disadvantage that when opened wide, the two pivot parts are unintentionally uncoupled. This makes the handling of the tool more difficult and can also provide a safety risk in the case of surgical interventions.

U.S. Pat. No. 5,197,879 discloses a pivot joint for scissor-like tools in the medical area which consists of two identically formed halves. Each half includes a guide recess and a guide rail, in the coupled state the guide rail of the one part engaging in the guide groove of the other part. The pivot joint can be uncoupled in a certain position of opening, the guide rails in said position of opening no longer engaging in the guide grooves. The disadvantage of said apparatus is that it can also result in unintentional uncoupling when opened wide.

SUMMARY OF THE INVENTION

Accordingly, an aspect of the invention is providing a pair of forceps or scissors which has a pivot joint, can be taken apart, has no small parts, has as few individual parts as possible, is easy to handle and avoids the above-described disadvantages.

This aspect is achieved by a pair of forceps or scissors as broadly described herein. Advantageous further developments are the object of the detailed embodiments described below.

Accordingly, the invention relates to a pair of forceps which includes a handle, a pivot joint and a jaw. In addition it has two forceps parts, each of which has two identically realized, releasably coupled, pin-less pivot joint elements, wherein the first pivot joint element has a first guide rail and a first guide recess, and the second pivot joint element has a second guide rail and a second guide recess, wherein the guide rails, which engage in an undercut of the guide recesses on the pivot joint elements, form a sliding guide for the pivot joint. The first pivot joint element has a first thickening element and the second pivot joint element has a second surface element, wherein the pivot joint elements are mounted in the coupled state so as to be rotatable about a central rotational axis in relation to one another between an end position and a safety position. In the safety position the first thickening element interacts with the second surface element such that the two pivot joint elements are jammed. In this case, the jamming can be over-pressed by increased force being expended.

The invention makes simple separation of the forceps parts possible and does not require any small parts such as screws or pins for this purpose. It is realizable in two parts and has a pivot joint which does not have a pin. As a result, effective and simple disinfection and cleaning, for example in an autoclave, is made possible. The guide recess can be developed in a very flat and wide manner such that in the medical area tissue remains and tissue fluid remains are easily able to be removed. As a result, bacteria and viruses are deprived of the ability to infect. By jamming the thickening element of the one pivot joint element with the surface element of the other pivot joint element, unintentional opening and uncoupling of the two pivot joint elements is prevented. This simplifies the handling of the tool in a considerable manner. In this way, the invention links the advantage of the uncouplability of the two forceps parts with a safe method of operation.

The apparatus has an open position in which the first and the second pivot joint elements are able to be released from one another or coupled together. No guide rail is arranged in a guide recess anymore in said open position. By means of rotation about the central axis, the guide rails engage in the guide recess and couple the first and the second pivot joint elements together. In addition, the apparatus is moved into the safety position as a result. In the safety position, the first and the second thickening elements are jammed with the first or second surface elements. Said jamming can be overcome by means of further rotation expending increased force. The apparatus moves into the end position by means of further rotation. In the end position, the jaw of the forceps or the blades of the scissors is or are closed. From the end position, the apparatus can only be opened so far until the safety position is achieved.

The pivot joint elements are preferably realized in a resilient manner. With the jaw closed and when an object is being held in the jaw, the pivot joint elements absorb part of the force exerted onto the control elements.

The two pivot joint elements preferably have in each case a slotted annular spring. The axis of the annular spring, in this case, coincides with the rotational axis of the pivot joint. The slot of the annular spring is arranged on the side on which the control elements of the tool are arranged. The annular springs develop their action in the end position. If the control elements are actuated in said position, in which the jaw of the forceps is closed, the slot of the annular spring is pressed together and the force is transmitted to the annular spring. As a result, a transmission of excessive force from the control elements to the closed jaw of a pair of forceps is prevented.

When the jaw holds an object, part of the force exerted onto the control elements is also transmitted to the annular spring. This allows the user, by slightly increasing the force expended onto the control element, to test whether the object to be gripped is already encompassed by the jaw.

Damage to the objects held by a pair of forceps can be avoided by said tactile feedback. This is advantageous in particular in the medical area when, for example, needles for sewing wounds are to be held by way of a pair of forceps. In addition, the advantage of the embodiment with the annular spring is that in the case of a rotation, less friction occurs between the two pivot joint elements than in the case of an embodiment without an annular spring. This increases the smooth-running of the tool in a considerable manner. In addition, additional surfaces which have to be cleaned are avoided.

By realizing both forceps parts in an identical manner, a cost-efficient production is made possible as the number of different parts is kept small. In addition, if the one forceps part is damaged or lost, the other forceps part can continue to be utilized, which has the advantage for the user that even in the case of the possible loss or damage of one forceps part, it is possible to continue utilizing the forceps in a cost-efficient manner.

The control elements are preferably provided with recesses in which the fingers are able to be positioned during use. As a result, the fingers are prevented from slipping. In this way, the manipulability of the tool is increased.

In a first embodiment of the invention, the guide rail is arranged on the edge of the annular spring. The thickening element is also arranged on the edge of the slotted annular spring. In addition, the thickening element is arranged separately from the guide rail. In this embodiment, the guide recess is arranged in two parts on the jaw element and on the control element.

In a further embodiment of the invention, the guide recess and the thickening element are arranged on the edge of the annular spring. In said embodiment the guide rail is arranged in two parts on the jaw element and on the control element.

In a further embodiment of the invention, the guide rail or the guide recess can have a thickening element. The thickening element, in this case, is arranged such that, in the safety position, it interacts with the surface element of the other pivot joint element and forms jamming.

BRIEF DESCRIPTION OF THE DRAWINGS

The invention is explained below as an example by way of an advantageous embodiment with reference to the accompanying drawings, in which, in detail.

DETAILED DESCRIPTION OF THE INVENTION

Figure 1:
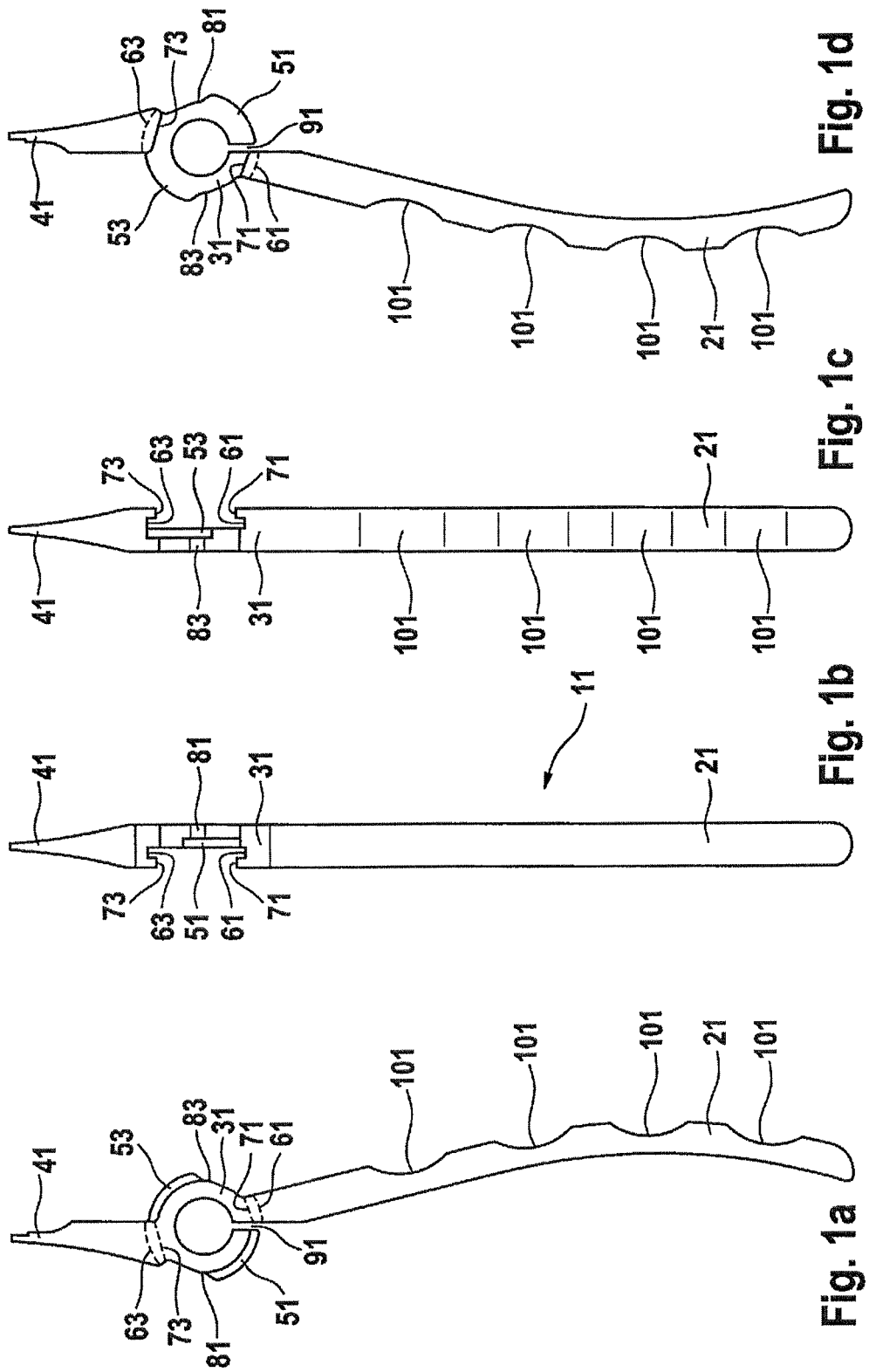
FIGS. 1 *a-d* show views from the front, from the left, from the right and from behind of a first forceps part.
Figure 2:
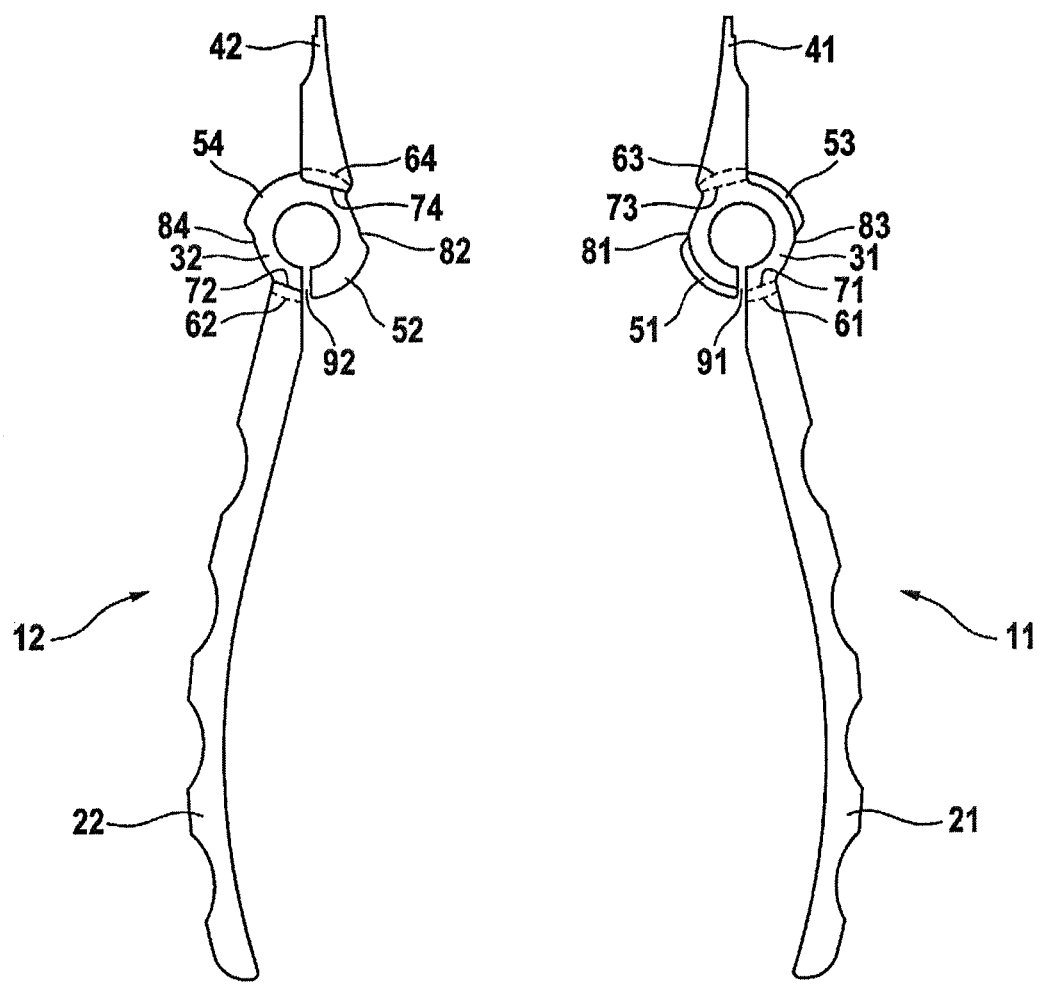
FIG. 2 shows forceps parts which have been released from one another.

The exemplary embodiment of the surgical forceps according to the figures includes a handle 2, a pivot joint 3, a jaw 4 and a first and a second forceps part 11, 12. The first forceps part 11 includes a first control element 21, a first pivot joint element 31 and a first jaw element 41. In the coupled state, when the first forceps part 11 is coupled with a second forceps part 12, a force can be transmitted via the first control element 21 and a second control element 22, which is arranged on the second forceps part 12, by means of the first pivot joint element 31 and a second pivot joint element 32 onto the first jaw element 41 and a second jaw element 42. The first and the second jaw elements 41, 42 can be developed either as scissor blades or as forceps jaws. The first pivot joint element 31 has a first guide rail 51 as well as a first thickening element 81. In one embodiment, the first thickening element 81 can be arranged on the guide rail 51 and in another embodiment it can be arranged next to the guide rail 51. In addition, the first pivot joint element includes a first guide recess 61 as well as a first surface element 71. In one embodiment, the first surface element 71 is arranged next to the first guide recess 61 and in another embodiment it is arranged in the guide recess 61.

The second forceps part 12 includes a second control element 22, a second pivot joint element 32 and a second jaw element 42. In addition, it has a second guide rail 52 as well as a second thickening element 82. The guide recesses 61, 62, in this case, form an undercut in which the guide rails 51, 52 are arranged in the coupled state, said guide rails forming a sliding guide for the pivot joint 3. In this case, the second guide rail 52 is arranged in the first guide recess 61 and the first guide rail 51 is arranged in the second guide recess 62. The guide rails 51, 52, which are mounted in the guide recesses 61, 62, bring about the coupling between the first forceps part 11 and the second forceps part 12 by means of the undercut. In addition, the guide rails 51, 52 and the guide recesses 61, 62 guide the two forceps parts 11, 12 during rotation about the central axis Z.

In addition, the first and the second pivot joint elements 31, 32 have a central axis Z which, in the coupled state, coincides with the rotational axis of the forceps parts 11, 12. The pivot joint elements 31, 32 are realized as annular springs, the annular springs having slots 91, 92 on the side of the pivot joint elements 31, 32 on which the control elements 21, 22 are arranged.

The curved faces of the annular spring are arranged in a plane at right angles to the axis Z. In this case, the first slot 91 of the first pivot joint element 31 is arranged on the first control element 21 and the second slot 92 of the second pivot joint element 32 is arranged on the second control element 22. During the coupling between the first pivot joint element 31 and the second pivot joint element 32, the two pivot joint elements 31, 32 are mounted so as still to be rotatable in relation to one another about the axis Z. The slots 91, 92 make spring action onto the control elements 21, 22 possible in the end position. As a result, introduction of increased force onto the control elements 22, 22 is absorbed such that the two jaw elements 41, 42 are pressed together in a manner which is only negligibly stronger.

Figure 3:
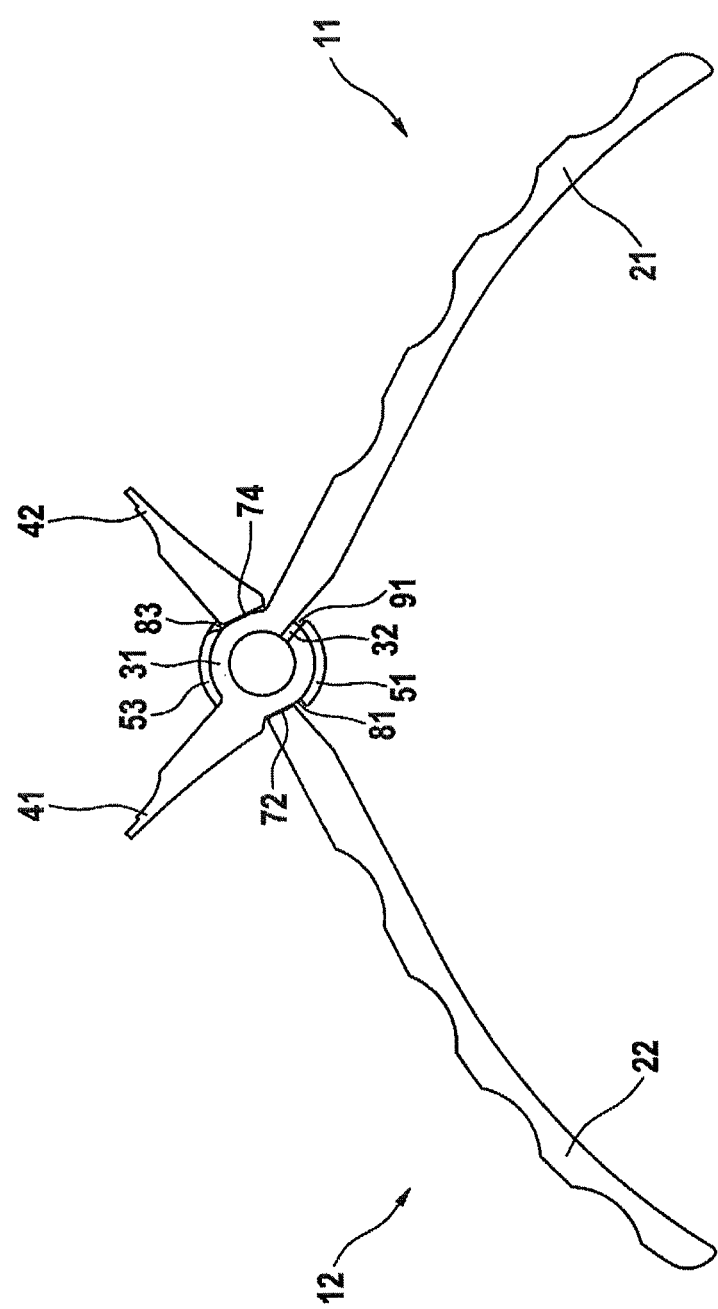
FIG. 3 shows the two forceps parts in the open position.

FIG. 3 shows the open position of the two forceps parts 11, 12. In said open position, the two forceps parts 11, 12 are arranged side by side so as to be releasable. The guide rails 51, 52 are not arranged in the guide recesses 61, 62. This make the release of the two forceps parts 11, 12 possible. In addition, the first thickening element 81 is not in contact with the second surface element 72. Neither is the second thickening element 82 in contact with the first surface element 71. By rotating the two forceps parts 11, 12 about the axis Z the guide rails 51, 52 are pushed into the guide recesses 61, 62. In this case, the first guide rail 51 of the first forceps part 11 is inserted into the second guide recess 62 of the second forceps part 12. The second guide rail 52 of the second forceps part 12 is inserted into the first guide recess 61 of the first forceps part 11. In addition, the first thickening element 81 of the first forceps part 11 comes into contact with the second surface element 72 of the second forceps part 12. The second thickening element 82 of the second forceps part 12 comes into contact with the first surface element 71 of the first forceps part 11.

Figure 4:
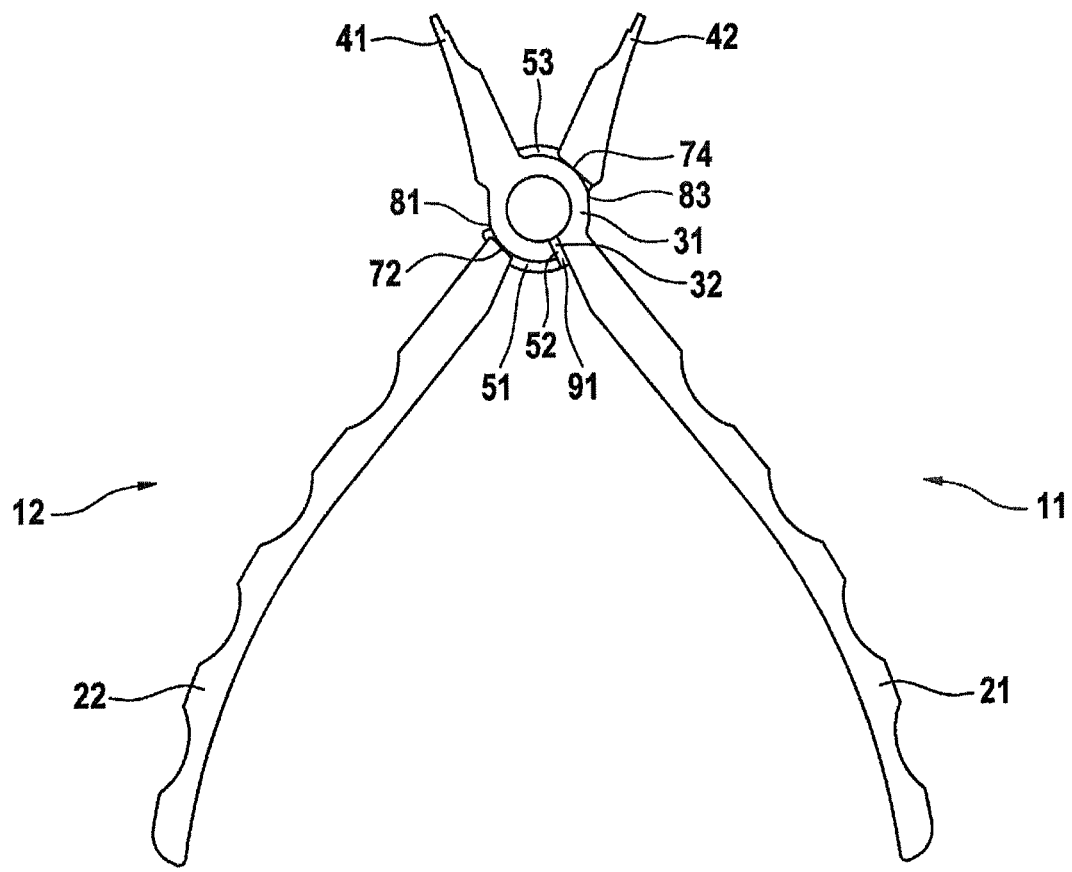
FIG. 4 shows the two forceps parts in the safety position.
Figure 5:
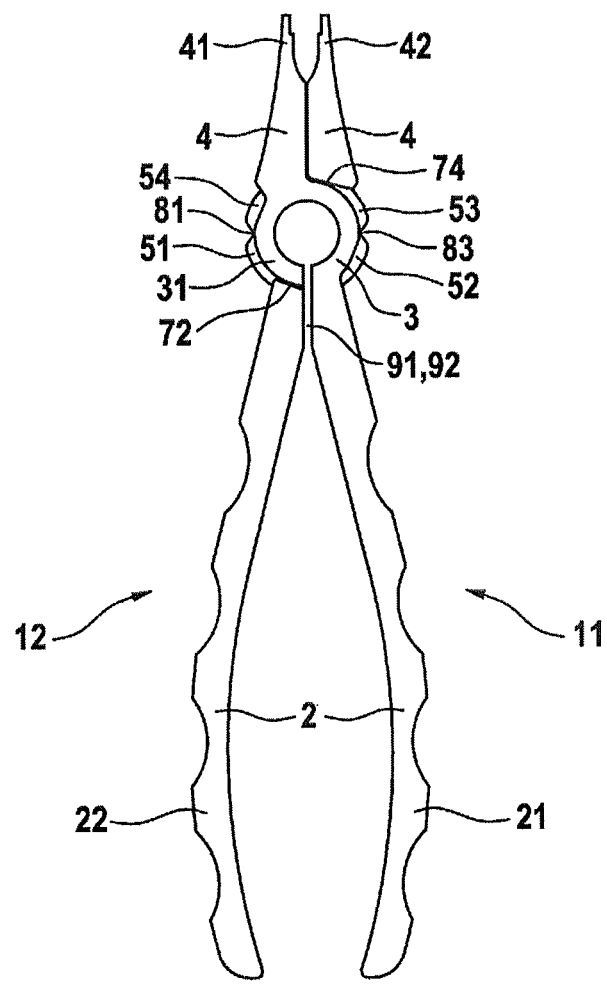
FIG. 5 shows the two forceps parts in the end position and FIG. 6 shows an enlarged representation of the pivot joint element.
Figure 6:
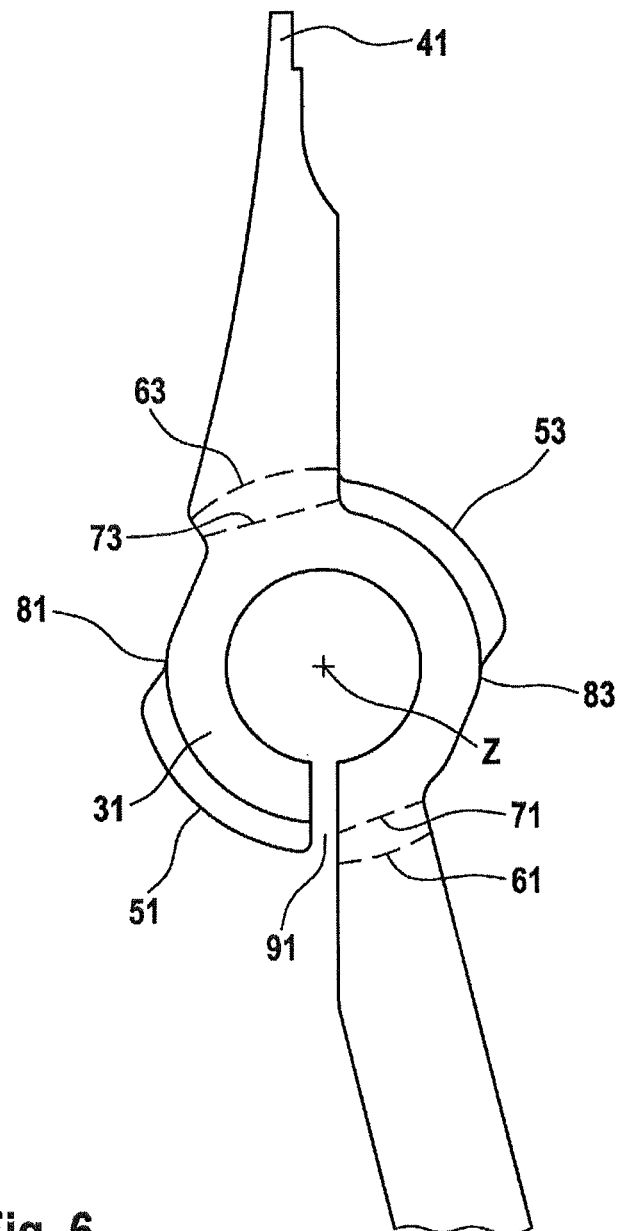

In this case, the safety position of the tool shown in FIG. 4 is achieved. In said position, the first thickening element 81 interacts with the second surface element 72 and the second thickening element 82 interacts with the first surface element 71 such that jamming occurs. As a result, rotation of the two forceps parts 11, 12 in relation to one another about the axis Z is made more difficult. It is only possible to achieve further rotation by expending increased force. If the rotation is continued further in such a manner that the first thickening element 81 no longer contacts the second surface element 72 and the second thickening element 82 no longer contacts the first surface element 71, further rotation is possible without increased expenditure of force as far as up to the end position shown in FIG. 5. From the end position, the two forceps parts 11 and 12 can only still be rotated in relation to one another in the direction of the safety position.

In an advantageous embodiment, the first forceps part 11 includes a first pivot joint element 31 with a first surface element 71, a third guide rail 53, a third thickening element 83, a third surface element 73 and a third guide recess 63. Accordingly, in said embodiment the second forceps part 12 includes a pivot joint element 32 with a second thickening element 82, a fourth guide rail 54, a fourth surface element 74 and a fourth thickening element 84 as well as a fourth guide recess 64. The third guide recess 63, the third guide rail 53, the third surface element 73 and the third thickening element 83 are arranged in such a manner that they proceed from a rotation of the first guide recess 61 or the first guide rail 51 or the first surface element 71 or of the first thickening element 81. The fourth guide recess 64, the fourth surface element 74 and the fourth guide rail 54 as well as the fourth thickening element 84 proceed from a rotation about the axis Z of the second guide recess 62 or the second surface element 72 or the second guide rail 52 or of the second thickening element 82. The guide rails 51, 52 and 53, 54 are in each case arranged on the outer surfaces of the annular springs. The guide rails 51, 52, 53, 54, in this case, are developed in such a manner that they just cover a maximum angle of 90° with reference to the axis Z.

In a coupled position, the third guide rail 53 of the first pivot joint element 31 is arranged in the fourth guide recess 64 and the fourth guide rail 54 of the second pivot joint element 32 is arranged in the third guide recess 63 of the first pivot joint element 31. In the safety position, the third thickening element 83 of the first pivot joint element 31 interacts with the fourth surface element 74. The fourth thickening element 84 of the second pivot joint element 32 interacts in said position with the third surface element 73 of the first pivot joint element 31. As a result, the expenditure of force, by way of which the two forceps parts 11, 12 are able to be rotated out of the safety position, is increased. This increases the safety of the handling of the tool in a considerable manner.

In a further advantageous embodiment, the two forceps parts 11 and 12 are identical. As a result, the production costs of the tool can be reduced. In addition, this has the advantage that if one forceps part 11, 12 is lost the respectively remaining forceps part is able to be combined with a third forceps part which is designed identically. The same applies in the case of any damage to one forceps part 11, 12. In addition, they can have recesses 101 for gripping by fingers, by means of which the fingers are prevented from slipping during operation.

The thickening elements 81, 82, 83, 84 can be arranged on the guide rails 51, 52, 53, 54 and the surface elements 71, 72, 73, 74 can be arranged in the guide recesses 61, 62, 63, 64. The thickening elements 81, 82, 83, 84 can also be arranged in the guide recesses 61, 62, 63, 64 and the surface elements 71, 72, 73, 74 can be arranged on the guide rails 51, 52, 53, 54.

The material, from which the first and the second forceps parts 11, 12 are produced, preferably has a non-corroding characteristic and only allows for a very limited colonization of bacteria and germs. Such types of materials are, for example, stainless steels, non-corroding alloys or also special plastics materials.

The invention claimed is:

1. A pair of forceps comprising a handle, a pivot joint with a rotational axis, a jaw, first and second releasably coupled forceps parts, an open position, an end position and a safety position between the open position and the end position, the first forceps part having a first pin-less pivot joint element, the second forceps part having a second pin-less pivot joint element, the first pivot joint element having a first guide rail and a first guide recess, the second pivot joint element having a second guide rail and a second guide recess, wherein the guide rails, which engage in an undercut of the guide recesses on the pivot joint elements, form a sliding guide for the pivot joint, the first pivot joint element has a first thickening element distinct from the first guide rail, the second pivot joint element has a second surface element, in the open position the first and the second pivot joint elements are able to be released from one another or coupled together, in the end position the jaw of the forceps is closed, and in the safety position the first thickening element interacts with the second surface element by jamming which can be over-pressed by an increased force being expended in order to continue rotational movement of the forceps parts around the pivot joint, the increased force comprising a second force greater than a first force, the first force capable of moving the forceps from the end position to the safety position but incapable of moving the forceps in the safety position.

2. The pair of forceps of claim 1, wherein the forceps parts are identical.

3. The pair of forceps of claim 1, wherein the first pivot joint element has a first surface element, a third guide rail, a third guide recess, a third surface element and a third thickening element, and wherein the second pivot joint element has a second thickening element, a fourth guide rail, a fourth guide recess, a fourth surface element and a fourth thickening element.

4. The pair of forceps of claim 3, wherein in the safety position one or more of the second thickening element interacts with the first surface element, the third thickening element interacts with the fourth surface element or the fourth thickening element interacts with the third surface element by jamming.

5. The pair of forceps of claim 3, wherein each of the guide rails cover a maximum angle of 90° with reference to a rotational axis of the pivot joint.

6. The pair of forceps of claim 1, comprising control elements having recesses for gripping by fingers.

7. The pair of forceps of claim 1, wherein the first pivot joint element is configured as a slotted annular spring having a first slot arranged on the handle.

8. The pair of forceps of claim 7, wherein the first thickening element is arranged on an edge of the slotted annular spring.

9. The pair of forceps of claim 8, wherein the first guide rail is arranged on an edge of the slotted annular spring and the first thickening element is arranged next to and separately from the first guide rail.

10. The pair of forceps of claim 8, wherein the first guide recess is arranged in an edge of the slotted annular spring and the first thickening element is arranged next to and separately from the first guide recess.

11. The pair of forceps of claim 7, wherein the first thickening element is arranged on the first guide rail.

12. The pair of forceps of claim 7, wherein the first thickening element is arranged in the first guide recess.

13. The pair of forceps of claim 1, wherein the second pivot joint element configured as a slotted annular spring having a second slot arranged on the handle.

14. The pair of forceps of claim 1, wherein said pair of forceps comprises a material which is corrosion-free and antibacterial, the material comprising a metal, an alloy or a plastics material.

* * * * *